United States Patent [19]

Cortes

[11] Patent Number: 5,326,346
[45] Date of Patent: Jul. 5, 1994

[54] LIGHT-CURED URETHANE DIMETHACRYLATE OCULAR PROSTHESIS

[75] Inventor: Aquileo L. Cortes, San Antonio, Tex.

[73] Assignee: Board of Regents, The University of Texas System, Austin, Tex.

[21] Appl. No.: 920,267

[22] Filed: Jul. 27, 1992

[51] Int. Cl.⁵ .............................................. A61F 2/14
[52] U.S. Cl. ....................................... 623/4; 623/901
[58] Field of Search ...................... 623/4, 901; 606/107

[56] References Cited

U.S. PATENT DOCUMENTS

| | | |
|---|---|---|
| 303,726 | 8/1884 | Hamecher . |
| 1,993,121 | 3/1935 | Travers . |
| 2,391,305 | 12/1945 | Galeski . |
| 3,937,680 | 2/1976 | de Carle . |
| 4,396,377 | 8/1983 | Roemer et al. . |
| 4,396,476 | 8/1983 | Roemer et al. . |
| 4,425,094 | 1/1984 | Tateosian et al. . |
| 4,514,174 | 4/1985 | Dougherty et al. . |
| 4,544,625 | 10/1985 | Ishimaru et al. . |
| 4,551,486 | 11/1985 | Tateosian et al. . |
| 4,615,665 | 10/1986 | Tateosian et al. . |
| 4,698,373 | 10/1987 | Tateosian et al. . |
| 4,892,478 | 1/1990 | Tateosian et al. . |
| 4,968,725 | 11/1990 | Mukai et al. . |
| 5,171,265 | 12/1992 | Kelley .................................. 623/4 |

FOREIGN PATENT DOCUMENTS

| | | |
|---|---|---|
| 0126866 | 5/1984 | . |
| 0142172 | 5/1985 | European Pat. Off. . |
| 0014515 | 6/1990 | European Pat. Off. . |
| 0427300 | 5/1991 | European Pat. Off. . |
| 4011053.2 | 10/1991 | Fed. Rep. of Germany . |
| 8900029 | 1/1989 | PCT Int'l Appl. ................. 606/107 |

OTHER PUBLICATIONS

Andreopoulos, A. G. et al., "Repairs with Visible Light-Curing Denture Base Materials," *Quintessence International*, 22:703–706, 1991, published in USA.
Triad ®, VLC Provisional Crown & Bridge Material, Dentsply. Int'l. Inc., York, Pa., 1986, published in USA.
Eichhold, W. A., et al., "Denture Base Acrylic Resins: Friend or Foe?", *Compendium of Continuing Education Dent.*, vol. XI, 12:720–725, published in USA.
Hayden, W. J., "Flexural Strength of Microwave-Cured Denture Baseplates," *General Dentistry*, Sep.-Oct. pp. 367–371, 1986, published in USA.
Helpful Recommendations for Denture Base Resins, L. D. Caulk Co., Dentsply. Int'l. Inc., Milford, Del., 1978, published in USA.
Hoefling, R. et al., "Processing of Ocular and Oral-Facial Prostheses with Microwave Irradiation," Fifth Annual American Anaplastology Assocation Meeting, University of Washington Dental School, Jun. 8–11, 1990, published in USA.
Kahn, Z., et al., "The Physical Properties of a Visible Light-Cured Temporary Fixed Partial Denture Material," *J. Prosthetic Dent.*, 60:543–545, 1988, published in USA.
Ogle, R. E., et al., "A New Visible Light-Cured Resin System Applied to Removable Prosthodontics," *J. Prosthetic Dent.*, 56:497–506, 1986, published in USA.
Rudd, K. D., et al., "Waxing and Processing," Chapter 9, *Dental Laboratory Procedures*, vol. 1, Complete Dentures, 2nd Ed., St. Louis: C. V. Mosby Co., 1986, published in USA.
Stungis, T. E., et al., "Hypersensitivity to Acrylic
(List continued on next page.)

Primary Examiner—Randall L. Green
Assistant Examiner—Mary Beth Jones
Attorney, Agent, or Firm—Arnold, White & Durkee

[57] ABSTRACT

An ocular prosthesis for use directly or as a component for an orbital prosthetic appliance to replace the eye piece consisting essentially of urethane dimethacrylate. Use of this acrylic resin polymerized with a visible light cure offers a clinically acceptable, clean and expedient way to construct this appliance. The method of construction is less time consuming compared to existing methods and utilizes a polymer with essentially no fugitive monomer or solvent. The prosthesis is a compatible alternative for patients experiencing methylmethacrylate sensitivity.

8 Claims, 16 Drawing Sheets

OTHER PUBLICATIONS

Resin," *J. Pros. Dent.*, vol. 22, No. 4, pp. 425–428, Oct. 1969, published in USA.

Dentsply® Traid ™, Denture System Technique Manual, Dentsply. Int'l. Inc., York, Pa., 1984, published in USA.

Srinivasan, B. D., et al, "Giant Papillary Conjunctivitis with Ocular Prostheses," *Arch Ophthalmol.*, 97:892–895, 1979, published in USA.

U.S. Department of Labor, Occupational Safety & Health Administration, Material Safety Data Sheet Nov. 1977, with accompanying OSHA communication regarding methyl methacrylate, May, 1986, published in USA.

Cain, J. R., "Custom Ocular Prosthetics," *Journal of Prosthetic Dentistry*, 48(6):690–694, 1982, published in USA.

Joneja, O. P., et al. "Orbital Prostheses," *J. Prosthes. Dent.*, 36(3):306–311, 1976, published in USA.

Danz, W., "Ancient and Contemporary History of Artificial Eyes," date, journal and place of publication unknown.

"Synthetic Resins: Denture Base Materials," Chapter 11, date, journal and place of publication unknown.

Soll, D. B., "The Anophthalmic Socket," *American Academy of Ophthalmology*, 89(5):407–423, 1982, published in USA.

Curley, R. K., et al., "Contact Sensitivity to the Amide Anesthetics Lidocaine, Prilocaine, and Mepivacaine," *Arch Dermatol.*, 122:924–926, 1986, published in USA.

Allen, L., and Bulgarelli, D. M., "The Painting Shell for Artificial Eyes," Iowa Eye Prosthetics, Inc., pp. 14–18, date and place of publication unknown.

Allen, L., and Webster, H. E., "Modified Impression Method of Artificial Eye Fitting," *American Journal of Ophthalmology*, 67(2):189–218, 1969, published in USA.

Bulgarelli, D., and Allen, L., "Prosthetics, Problems and Their Management," *American Academy of Opthalmology*, 1981 Instruction Section, Course 81, published in USA.

"Certification, Registration and Recertification," *National Examining Board of Ocularists*, published in USA.

Allen, L. et al., "Care of Your Artificial Eye and Related Information," *Iowa Eye Prosthetics, Inc.*, published in USA.

Prince, J. H., *Recent Advances in Ocular Prosthesis*, E. & S. Livingstone Ltd., publishers, 1950, published in Great Britain.

Prince, J. H., *Ocular Prosthesis*, E. & S. Livingstone Ltd., publishers, 1946, published in Great Britain.

"Registry of Toxic Effects of Chemical Substances," *U.S. Department of Health and Human Services*, 1985–86, published in USA.

Allen L., "Plastic Artificial Eyes," *Iowa Eye Prosthetics, Inc.*, published in USA.

"Material Safety Data Sheet," Aldrich Chemical Co., Aug. 31, 1989, published in USA.

Triad VLC Material Properties, ADA Specification No. 12 Tests, USA.

Material Safety Data Sheet for Triad VLC Provisional Material, published in USA.

Ludwig, K., et al., "Release and Elimination of Methylmethacrylate Monomer after Intraocular Lens Implatation," *Graefe's Archive for Clinical and Experimental Ophthalmology*, 225(6):426–428; published in Germany.

Anderson, R. L., and Stasior, O. G., "Self-Curing Methyl Methacrylate: Is It Safe?", *Ophthalmic Surgery*, 7(4):28–30, 1976, published in USA.

LIGHT-CURED URETHANE DIMETHACRYLATE OCULAR PROSTHESIS

BACKGROUND OF THE INVENTION

The present invention relates to an ocular prosthesis for use directly or as a component of an orbital prosthetic appliance to replace an eye.

CONVENTIONAL OCULAR CONSTRUCTION

The construction of ocular prostheses has been a practiced "art" since Babylonian times. These artificial eyes were made with precious stones, precious metals, and other materials (Gordon B., *Annals of Medical History*, 1940). Pare, A. (Cimbroise, Paris, Orubres, 1561, 648–650), Haug P. A. (*Ypobrepharo Tubingen, Marz* 1749) and Heister L, (Von Kunstlicher Augen S. 1752, 581–582) have recorded cases of the manufacture and clinical delivery of oculars. Trester W. (*J. Am. Soc. Ocularists*, 1982 5–13) describes Müeller's artificial eyes constructed out of glass using methods that are still technologically sound by present standards. During the period of World War II, Stanley F. Erff, and other military research associates developed an MMA (methyl-methacrylate) ocular appliance, (Coates J. B., *Surgery in World War II*, 1957). Methyl methacrylate has been the material of choice because it was thought to offer the most optimum prosthetic and clinically biocompatible results to date.

The conventional procedure for the construction of an ocular prosthesis involves steps similar to those used in the processing of a heat-cured denture. These steps include investing, boiling out, packing and curing under pressure inside brass flasks in a temperature controlled curing unit for polymerization to occur (Morrow et al., *Dental Laboratory Procedures*, 1986).

After the initial impression of the defect is taken, the impression is poured and allowed to set in dental gypsum. During this time, an iris disk is painted to match the opposing natural eye. This process and the luting of the pupil button takes approximately 30 minutes. When the impression is separated and a positive of the defect is obtained, a wax-conformer is constructed to be fitted on the patient (this conformer is a wax replica of the eventual eye). This procedure normally takes 15–30 minutes. At this point the iris and pupil button are adapted to the conformer to achieve facial symmetry. Following this step, the wax conformer is invested and boiled out. The entire conformer is encased in dental gypsum, eliminated wax leaves a void which is packed with acrylic. This process, when accomplished by a very experienced practitioner using speed catalysts, could take 2–3 hours. This portion of the ocular is referred to as the scleral portion. When this scleral portion is cured, it is fitted to the patient and repainted to match the healthy eye. This scleral portion of the ocular is then taken through the same procedures as before, since a clear shell resembling the cornea is added to surround the ocular. This further procedure will also take approximately 2–3 hours. The ocular is then finished, smoothed, polished, and inserted into the patient.

Using all short cuts with this technology, an ocular prosthesis can be finished in 7–9 hours. However, one of these short cuts is a 2.5 hour heat cure procedure which may yet allow some catalyst monomer to remain as a free agent. One can further reduce the amount of this free monomer by boiling the material for an extra ½ hour, however, some of it still remains and has a tendency to irritate tissue. The manufacturer's instructions recommend that polymethyl-methacrylate be processed using a long heat cure (8–9 hours at 168 degrees F.). Technicians in the field, however, use a short cure procedure of 2,5 hours.

The present invention describes the construction of an ocular prosthesis from light-cured materials which do not contain methyl-methacrylate. Therefore, there is essentially no residual monomer to cause tissue irritation and the length of time to construct the prosthesis is shortened to about 2 hours.

Ruddet al., (*Dental Laboratory Procedures*, 1986) discuss the processing procedures for constructing dentures. Andreopoulos et al., (*Quintessence International*, 703–706, 1991) discuss the visible light-curing (VLC) resin system as used for denture repairs. The material was introduced into the dental market in 1983 and comprises a urethane dimethacrylate matrix with acrylic resin copolymer and a microfine silica filler accompanied with camphoroquinone amine as the photoinitiator. Curing is accomplished with visible light (400 to 500 nm). The present invention uses this resin system for the construction of the ocular prosthesis.

Eichhold et al., (*Compendium of continuing education Dent.*, 720–725) reviews the advantages and disadvantages of dentures based on acrylic resins and mentions light cure as a possible curing method. The abstract by Hoefling et al., (Fifth Annual American Anaplastology Association Meeting, 1990) describes the construction of ocular prostheses in which the polymerization of the methyl methacrylate is accomplished with microwave irradiation.

Hayden (*General Dentistry*, 367–371, 1986) describes the time saving factor in the use of microwave irradiation for the curing of prosthetic appliances. Ogle et al., (*J. Prosthetic Dent.*, 497–506, 1986) discuss the use of the Triad VLC resin technology in dentistry. Khan et al., (*J. Prosthetic Dent.*, 543–545, 1988) suggests that Triad TM VLC (visible light curable) material could be advantageous for those patients sensitive to poly (methylmethacrylate) since the Triad TM VLC material does not contain this chemical.

The pamphlets, (Triad TM, VLC Provisional Crown & Bridge Material, 1986; Helpful Recommendations for Denture Base Resins, 1978; Dentsply® Triad TM, Denture System Technique Manual 1984) by the manufacturer of the Triad® VLC resins, describe the techniques for using the resins in dentures, provisional crowns and bridges.

A German patent No. 4,011,053, issued Oct. 10, 1991 relates to a visible light cured artificial eye lens material for cataract operations consisting of a liquid monomer which is injected directly into the empty capsular sac of the eye and polymerized with light of 400–500 nm wavelength using the photoinitiator, camphorquinone. The monomer is fully tolerable to the tissue of the capsular sac. U.S. Pat. No. 3,937,680 relates to a hydrophilic terpolymer suitable for manufacture particularly into contact lenses.

U.S. Pat. No. 4,968,725 to Mukai et al. discloses dental adhesive compositions consisting of a urethane prepolymer containing one or more isocyanate groups, a radical-polymerizable unsaturated monomer and a photopolymerization initiator. The urethane prepolymer with isocyanate may be urethane dimethacrylate and the unsaturated monomer rapidly hardens the urethane dimethacrylate layer by exposure to light in the presence of a photoinitiator. One skilled in the art would see that the materials disclosed in this patent are similar to the materials used by the present inventor in the construction of an ocular prosthesis and thereby could be used in place of the VLC gel materials. The contents of U.S. Pat. No. 4,968,725 are incorporated by reference herein.

U.S. Pat. Nos. 4,551,486, 4,892,478, 4,615,665, 4,698,373 and 4,425,094 to Tateosian et al., 4,514,174 to Dougherty et al., 4,396,476 and 4,396,377 to Roemer et al., and European patents 14,515 to Roemer et al., 427,300, 142,172 and 126,866 to Tateosian et al., all to Dentsply Research and Development Corporation or Dentsply International, Inc., disclose compositions or methods of making and using compositions in dental appliances; the contents of these patents are incorporated by reference herein.

U.S. Pat. No. 4,544,625 to Ishimaru also describes urethane dimethacrylate and is incorporated by reference herein.

It is estimated that ocular prostheses are needed in about 30 cases a month of enucleations that occur due to cancer in a city the size of San Antonio. Additionally, that many cases occur per month due to accidental physical injury or trauma.

The advantages of replacing the heat-curable poly (methylmethacrylate) resins conventionally used for ocular prostheses with light-curable resins are apparent when the composite properties embodied in the very specialized resin produced by the Dentsply company are recognized. These include rapid curing character with low residual monomer, low deformation, castable/moldable in thin cross-section, ready cleanability and tissue tolerance to any possible residual monomer.

Those of skill in the ocular prosthesis arts, prior to the present inventor's conception, were apparently unaware of oral prosthesis technology.

SUMMARY OF THE INVENTION

The present invention relates to an ocular prostheses consisting essentially of polymerized urethane dimethacrylate. By polymerized urethane dimethacrylate, we mean a cross-linked urethane dimethacrylate based interpenetrating polymer network or matrix containing low levels of microfine silica. Urethane dimethacrylate means VLC (visible light curable) provisional or clear gel materials available from Dentsply International, Inc. The invention also relates to an ocular prostheses comprising polymerized urethane dimethacrylate, silica and acrylic resin beads.

A further aspect of the invention is an ocular prostheses comprising a sclera made from light-cured urethane dimethacrylate, silica, acrylic resin beads and a photoinitiator. By sclera we mean the major portion of the ocular, predominantly a whitish color, upon which are placed the iris and pupil disks and which is coated with a clear tissue bearing surface or corneal shell. Said light-curable urethane dimethacrylate, silica, acrylic resin beads and a photoinitiator is a VLC material obtained from Dentsply International, Inc. This VLC material has a tradename Triad TM and is cured or hardened by blue light (400-500 mm) from a high intensity quartz halogen lamp in a Triad TM curing unit.

A further embodiment of the invention is an ocular prostheses comprising a sclera made of light-cured VLC provisional material and a corneal shell made of light-cured VLC clear gel material. Light of wavelength into the ultraviolet region would be effective also for curing of these materials. Another aspect of the present invention is a method of constructing an ocular prostheses comprising the construction of the scleral portion made of VLC provisional material, adhering an iris disc and a pupil ocular button to the sclera portion and coating the composite with VLC clear gel material to construct a corneal shell. This method of construction of the sclera portion, the adhering of an iris disc and pupil button and the coating of the composite includes at least one light-curing step.

A further aspect of the present invention is a method of constructing an ocular prostheses for a patient comprising constructing a master cast, placing a thin layer of VLC clear gel in the master cast, curing the clear gel in the cast to form a clear tissue bearing surface, adapting provisional VLC material to the tissue bearing surface, curing adapted provisional material to form a sclera, trimming the sclera to fit a patient, trimming the solera for iris placement at a position of desired pupil placement, emplacing and curing a pupil disk and an iris disk, painting the sclera a desired color, emplacing colored rayon fibers at positions resembling blood vessles of the patient's other eye to produce a composite, covering the composite with clear gel and curing the clear gel.

This method takes significantly less time than that required by existing technology. The invention will have greater clinical acceptance than existing prosthetic devices since the composition does not contain a known irritant, poly (methylmethacrylate).

DETAILED DESCRIPTION OF THE PREFERRED EMBODIMENTS

Figure 1:
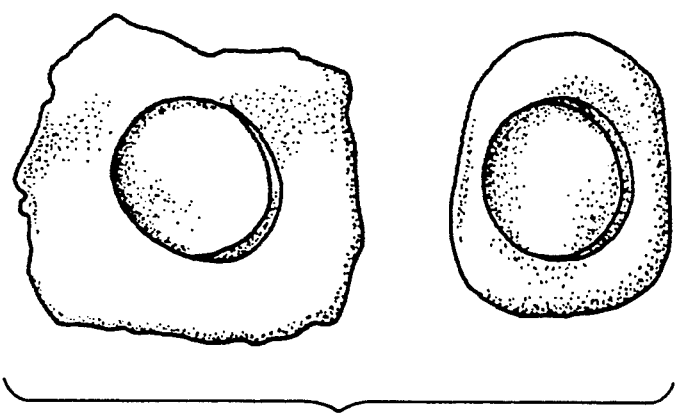
FIG. 1. Impression of existing ocular for the benefit of custom tray construction.
Figure 2:
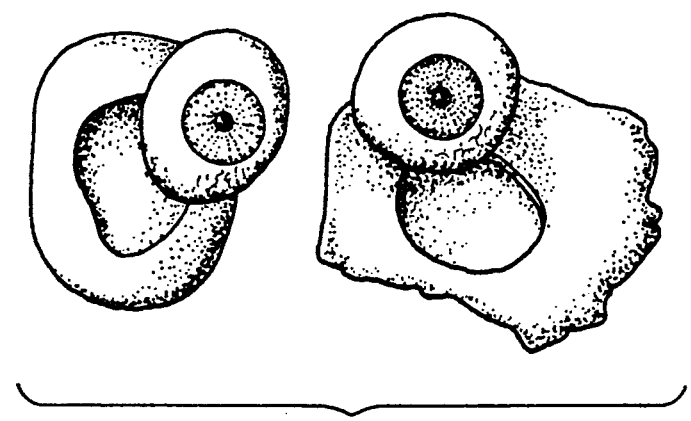
FIG. 2. Matrix material used is a silicone called Formasil II.
Figure 3:
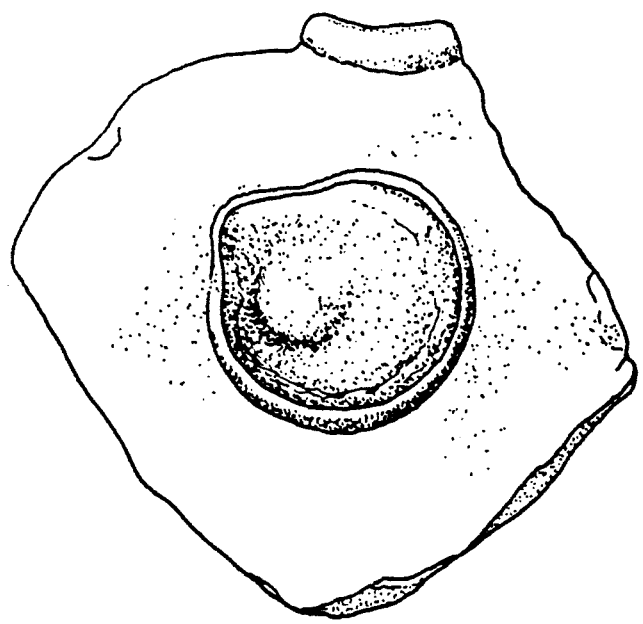
FIG. 3. Custom tray material poured into matrix and light cured.
Figure 4:
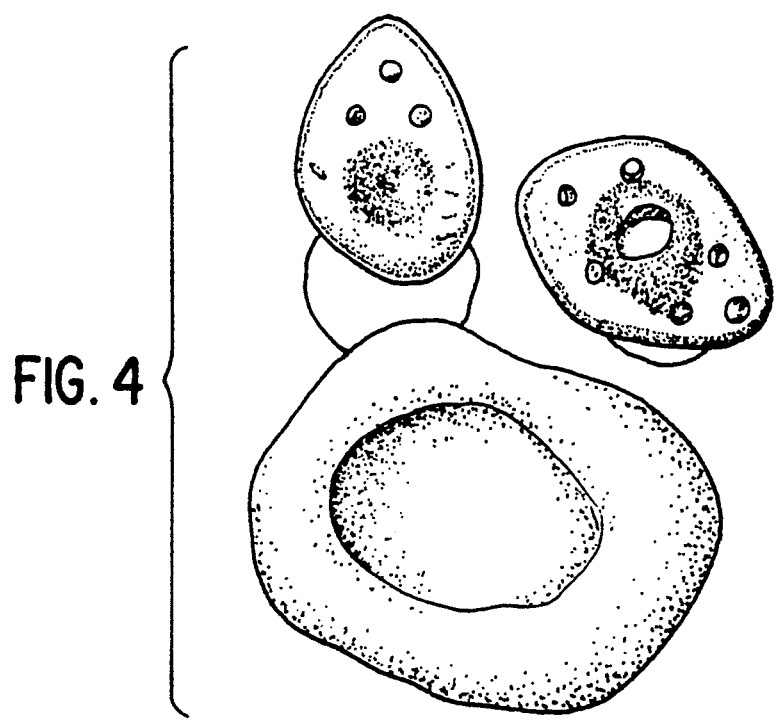
FIG. 4. Custom tray finished and perforated for retention.
Figure 5:
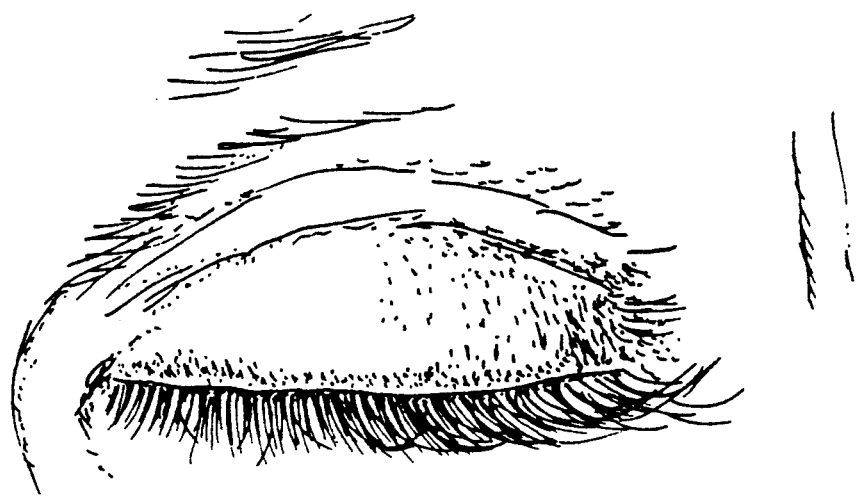
FIG. 5. Picture of defect without prosthesis (ocular).
Figure 6:
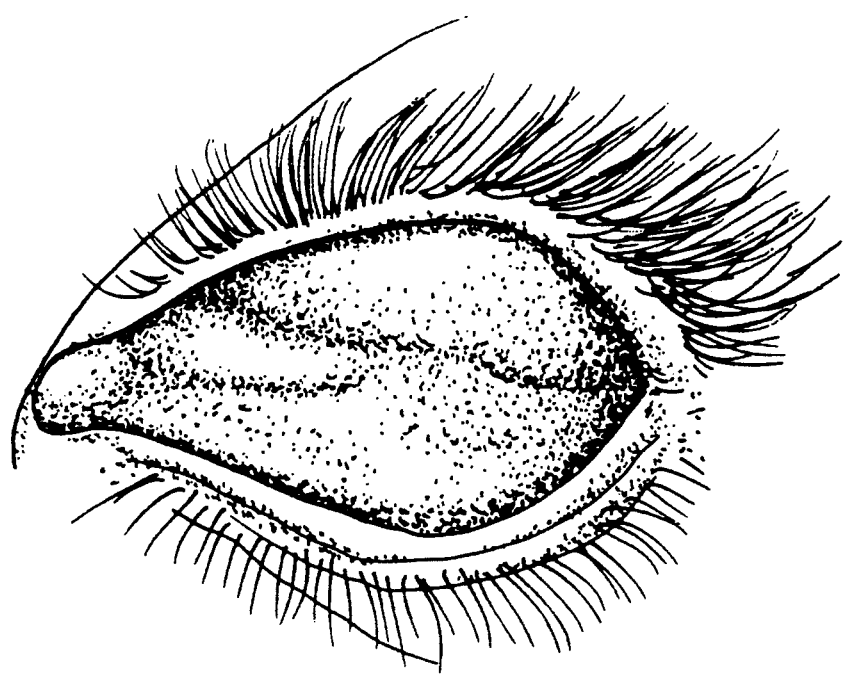
FIG. 6. Picture of tissue bearing defect for ocular prosthesis.
Figure 7:
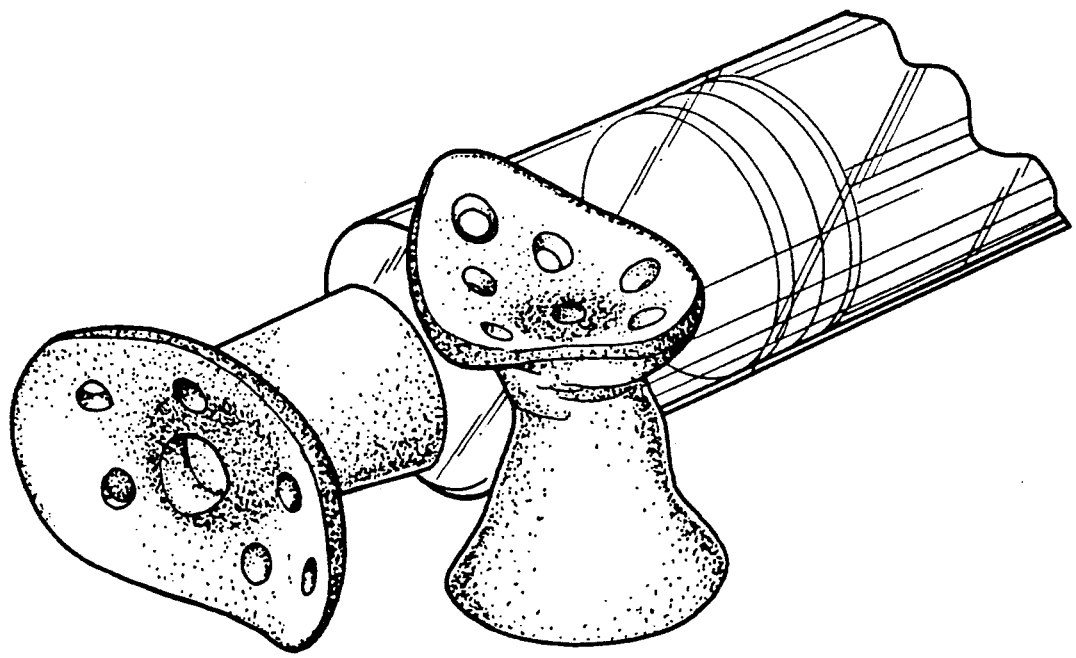
FIG. 7. Syringe to be utilized for defect impression.
Figure 8:
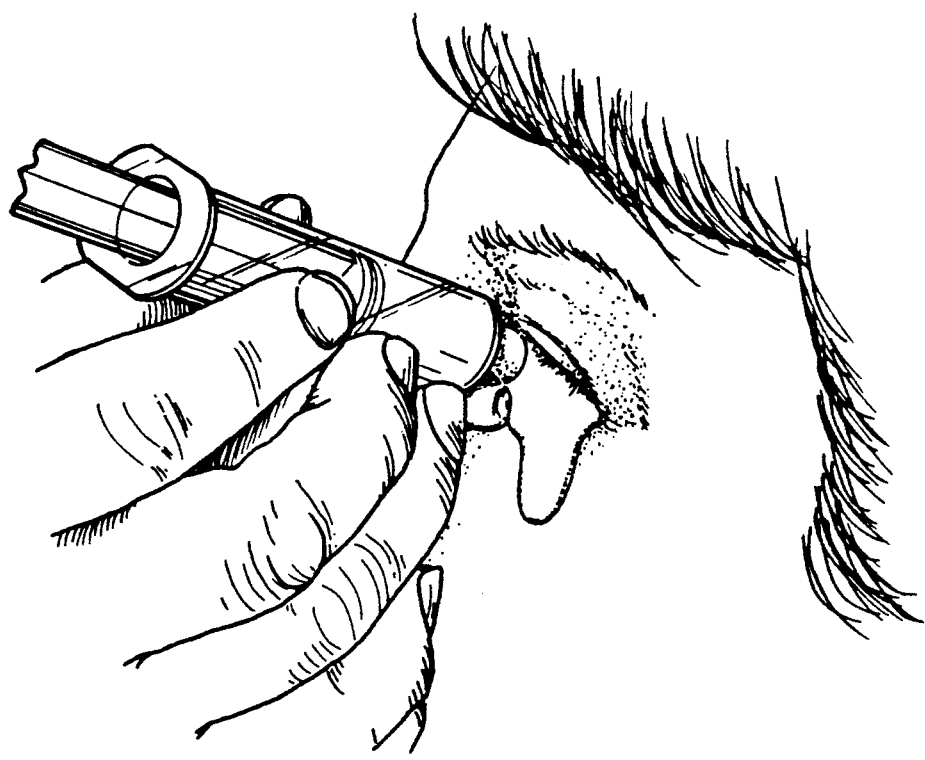
FIG. 8. Impression taken with ophthalmic alginate (non-irritating)
Figure 9:
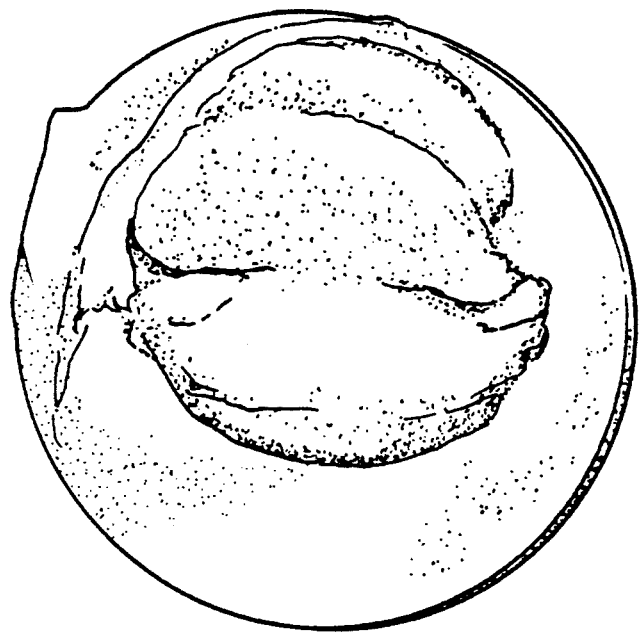
FIG. 9. Impression poured and master cast captured.
Figure 10:
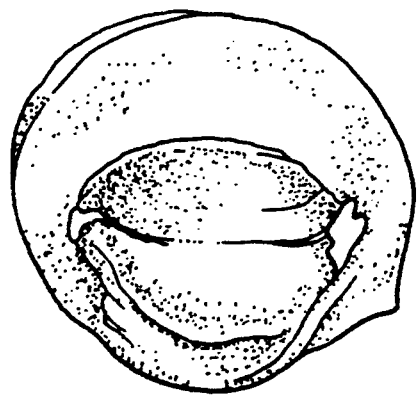
FIG. 10. Undercuts blocked out.

The ocular prosthesis of the present invention consists essentially of urethane dimethacrylate. Use of this acrylic resin polymerized with a visible light cure offers a clinically acceptable, clean and expedient way to construct this appliance. The method of construction is less time consuming compared to existing methods and utilizes a polymer with essentially no fugitive monomer or solvent. The prosthesis is a compatible alternative for patients experiencing methyl-methacrylate sensitivity.

The present invention uses visible light-cure (VLC) resin technology developed in the dental arts by Dentsply Research and Development Corp., Milford, Del. and described as interpenetrating polymer network compositions. U.S. Pat. No. 4,551,486 to Tateosian et al. is specifically incorporated by reference herein. This patent describes hardenable dental compositions comprising a blend of components which, when combined in certain proportions and permitted to age or mature, produce a blend that is moldable into prosthetic dentures and other dental devices. The blend is formed by combining a crosslinked polymer, crosslinking oligomers capable of addition polymerization, and an inorganic filler and/or an initiator and/or a monofunctional monomer, and by allowing said combination to age or mature. The crosslinked polymer is in the form of discrete particles having average diameters ranging from about 0.001 micron to about 500 microns. Preferably, at least 50 percent by weight of said particles have diameters less than about 150 microns, and more preferably, less than 100 microns. If desired, a mixture of two or more different crosslinked polymers may be used. A characteristic of the crosslinked polymer is that it will be insoluble in, but will be swollen by the liquid components used in the preparation of the blend.

The liquid polymerizable component of the compositions is one or more multifunctional oligomers having the capacity to swell the particles of crosslinked polymer.

It has been discovered that the relative proportions of the components of the blend are critical in preferred embodiments to the attainment of the desired properties in the unhardened state including slump resistance, packability, freedom from tackiness, penetration, flow, viscosity stability, and modelability. Also, the relative proportions of components are critical to the attainment of the desired properties in the final hardened or cured product produced therefrom, notably flexural fatigue, transverse strength, wear resistance, impact resistance, resistance to solvents, stain resistance, thermal stability, and hydrolytic stability. Thus, it has been discovered that blends of from about 10 to about 70 weight percent of the crosslinked polymer, from about 10 to about 70 weight percent of multifunctional oligomers, from about 3 to about 80 weight percent of inorganic filler, and less than about 2 weight percent of polymerizable monomer, together with minor amounts of initiator and in some cases activator or accelerator for the initiator, provide blends which are particularly useful in the production of denture bases characterized by properties far superior to those of conventional systems not used in the art.

Preferably, the multifunctional vinyl crosslinking composition or agent or multifunctional crosslinking oligomer capable of addition polymerization is preferably present in an amount of 10 to 70 weight percent, more preferably 20 to 60, and most preferably 30 to 65 weight percent. Preferably, the crosslinked polymer in the form of discrete particles is present in an amount of 3 to 70 weight percent, more preferably 5 to 70, and most preferably 8 to 55 weight percent. The inorganic filler is preferably present in the amount of 3 to 80 weight percent, more preferably 5 to 50 and most preferably 8 to 30 weight percent. The most preferred ranges are especially preferred for the preferred denture base composition.

The following description introduces a method of constructing an ocular prosthesis utilizing urethane dimethacrylate resins polymerized with a visible light cure. The method eliminates investing and packing because the materials themselves are a cross-linked urethane dimethacrylate that cures using a VLC curing unit. The scleral portion of this appliance is made out of the tooth colored VLC provisional material, which is available in various shades of color to match the scleral shade of the other eye. The iris disk and pupil ocular button are the same components used conventionally, and the corneal clear shell is composed of the VLC clear gel material.

The entire process takes about 2 hours and the only contact that this prosthesis has with polymethyl methacrylate is during the painting of the iris and the sclera. This procedure virtually eliminates the use of methyl-methacrylate monomer which contains the initiator benzoyl peroxide and the construction of the ocular prostheses can be accomplished from impression to clinical delivery within 2 hours.

The following examples are presented to describe specific preferred embodiments and utilities of the present invention and are not meant to limit the present invention unless otherwise stated in the claims appended hereto.

EXAMPLE 1

The Visible Light-Cure (VLC) Resin Technology

The present invention uses visible light-cure (VLC) resin technology developed for use in removable prosthodontics. The VLC resin denture base material is developed by Dentsply International, Inc., York, Pa. and is marketed under the tradename Triad TM.

An important component of the system is a curing unit that emits intense collimated shielded light from quartz halogen lamps that are concentrated in the shorter blue 400 to 500 nanometer (nm) wavelength spectrum of visible light. High-intensity light results in deep polymerization of the material to a depth of 5 to 6 mm. The unit contains a rotating platform that is elevated to a chamber where the soft uncured material is polymerized. Triad TM material is similar to light-cured composites but uses an organic rather than inorganic filler. The material is composed of a matrix of urethane dimethacrylate plus small amounts of microfine silica to control theology. The filler consists of acrylic resin beads of varying sizes that become part of an interpenetrating polymer network structure when cured. Polymerization of high molecular-weight acrylic resin monomers contained within the matrix is initiated with a camphoroquinoneamine photoinitiator. Air inhibition of the surface layer polymerization is prevented by applying an air-barrier coating before final polymerization. The material is manufactured in sheets and ropes and packaged in opaque plastic envelopes to prevent contamination by light. Other photoinitiators well known to those of the skill in the art may substitute for the camphoroquinoneamine, etc.

Biocompatibility testing conducted by Findley Research, Inc. (Berkley, Mass.), Hazelton Biotechnologies (Vienna, Va.), and North American Science Associates (Northwood, Ohio) for Dentsply International, Inc. found the polymerized material to be nontoxic and even the unpolymerized material to be of very low toxicity. Toxicity of the unpolymerized material was determined to be less than that in available clinical denture liners containing acrylic monomer. The results of biocompatibility tests of ADA Specification No. 41 on polymerized Triad TM VLC resin material are:

1. Mucous membrane irritation study in hamsters by Findley Research, Inc.: VLC resin did not cause irritation to the hamster cheek and pouch.
2. Sensitization test (guinea pig maximization) by Findley Research, Inc.: VLC resin caused weak skin sensitization reactions. The uncured material caused mild skin reactions.
3. *Salmonella typhimurium/mammalian* microsome preincubation assay (Ames test) by Hazelton Biotechnologies: VLC resin was nonmutagenic.
4. Cytotoxicity by agar overlay assay by North American Science Associates: VLC resin was not cytotoxic to L929 mouse fibroblast cells. The uncured material gave a 3 mm zone of lysis whereas the uncured methylmethacrylate lysed all cells in the petri dish.

Some of the advantages ascribed to the VLC resins are accuracy of fit, superior strength, complete polymerization without residual compounds, absence of free methyl-methacrylate, color stability, ease of fabrication, and ease of manipulation.

While the ocular prosthesis of the present invention is made using the Triad TM VLC Dentsply materials, one skilled in the art would recognize that other possible materials, especially those described in patents issued to Dentsply and to Mukai et al., (listed in the background section) may be usable for the construction of the ocular prosthesis of the present invention.

In particular, a composition may contain the ingredients of Mukai et al. as follows.

Urethane dimethacrylate has the general formula:

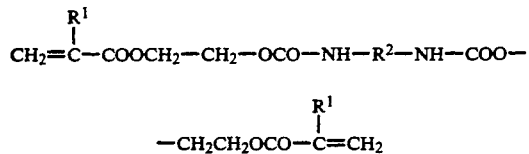

where $R^1$ is a hydrogen atom or a methyl group, and $R^2$ is an alkylene group of 1 to 8 carbon atoms, or

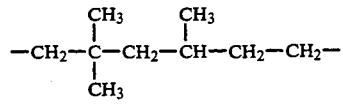

Specific examples thereof include di(acryloxyethyl)-dimethylene diurethane, di(methacryloxyethyl)-dimethylene diurethane, di(acryloxyethyl)tetramethylene diurethane, di(methacryloxyethyl)-tetramethylene diurethane, di(acryloxyethyl)-trimethylhexamethylene diurethane, and di(methcryloxyethyl)-trimethylhexanmethylene diurethane. Especially preferred is the urethane dimethacrylate of the structural formula:

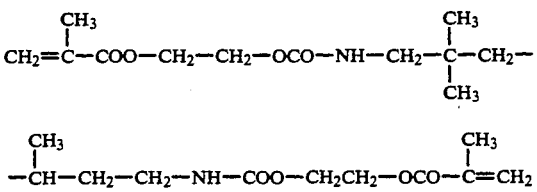

having the chemical name, N,N-bis(2-methacryloxyethoxycarbonyl)-1,6diamino-2,2,4-trimethyl hexane.

In general, urethane dimethacrylate of the present invention may be obtained by reacting a polyol compound with a polyisocyanate in such a way that part of the isocyanate groups remain unreacted. The polyol compound used for this purpose may be selected from polyether polyols and polyester polyols. In particular, urethane dimethacrylate is the reaction product of hydroxyethylmethacrylate and 2,2,4-trimethylhexyl-1,6-diisocyanate.

A radical-polymerizable unsaturated monomer is required to rapidly harden the adhesive layer by exposure to light in the presence of a photopolymerization initiator. For this purpose, there may be used any radical-polymerizable unsaturated monomer that does not interfere with the urethane dimethacylate. Useful unsaturated monomers include monofunctional and multifunctional unsaturated monomers.

Specific examples of useful monofunctional unsaturated monomers include ethylmethacrylate, propyl methacrylate, butyl methacrylate, pentyl methacrylate, hexyl methacrylate, 2-hydroxyethyl methacrylate, glycidyl methacrylate, benzyl methacrylate, vinyl acetate, styrene and acrylonitrile.

Useful bifunctional unsaturated monomers include for example, polyethylene glycol dimethacrylates. Specific examples thereof include ethylene glycol dimethacrylate, diethylene glycol dimethacrylate, triethylene glycol dimethacrylate, tetraethylene glycol dimethacrylate, pentaethylene glycol dimethacrylate, hexaethylene glycol dimethacrylate, heptaethylene glycol dimethacrylate, octaethylene glycol dimethacrylate, nonacethylene glycol dimethacrylate, and decaethylene glycol dimethacrylate.

The photopolymerization initiator may be selected from conventionally known visible light polymerization initiators. The compounds which can be used for this purpose are, for example, α-diketone compounds. Specific examples of useful α-diketone compounds include camphorquinone, benzil and diacetyl. Among others, camphorquinone is especially preferred because of its high polymerization activity.

In order to achieve desired excellent photopolymerizability, it is desirable to use a visible light polymerization initiator comprising a combination of a photosensitizer as described above and a reducing agent such as a tertiary amine. Specific examples of useful tertiary amines include aliphatic amines such as trimethylamine, triethylamine and tripropylamine; and aromatic amines such as isoamyl 4-(N,N-dimethylamino)-benzoate, hexyl 4-(N,N-dimethylamino)benzoate, heptyl 4-(N,N-dimethylamino)benzoate, octyl 4-(N,N-dimethylamino)benzoate, 4,4'-bis(dimethylamino)benzophenone, 4,4'-bis(diethylamino)benzophenone and 4,4'-bis(dibutylamino)benzophenone. Among others, aromatic tertiary amines are preferred. In particular, isoamyl 4-(N,N-dimethylamino)benzoate, 4,4'-bis(dimethylamino)benzophenone and 4,4'-bis(diethylamino)benzophenone are most preferred because excellent visible light polymerizing activity can be obtained by using them in combination with camphorquinone.

EXAMPLE 2

Construction of a Light-Cured Ocular Prosthesis Materials

Figure 11:
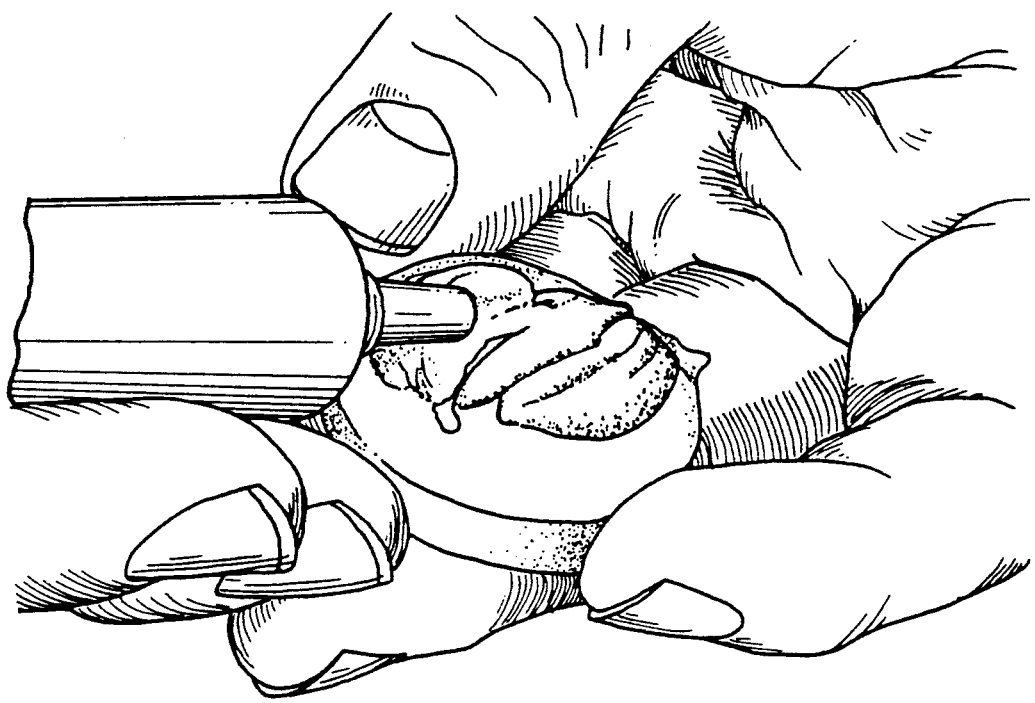
FIG. 11. Clear gel (Triad) poured into master cast (adapted from tube).
Figure 12:
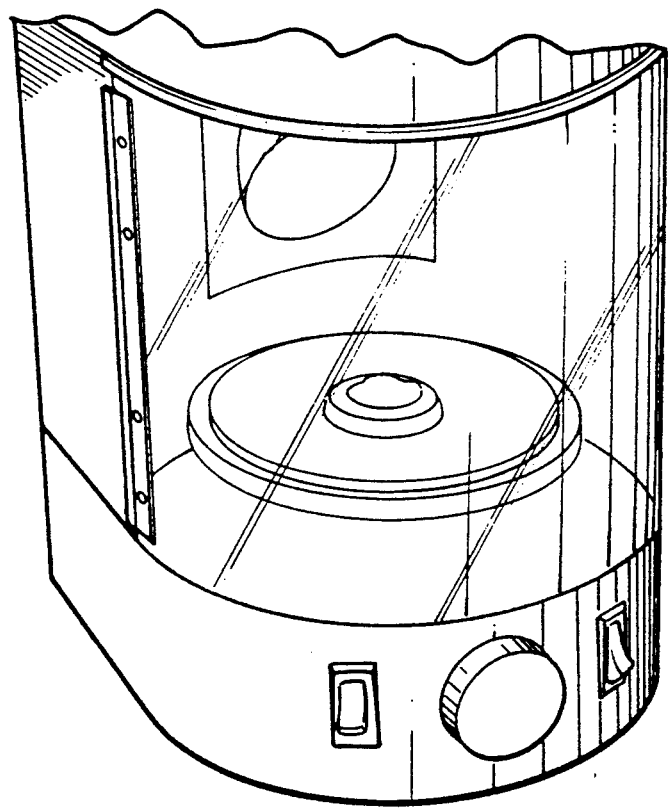
FIG. 12. Cured in light curing unit for recommended time.
Figure 13:
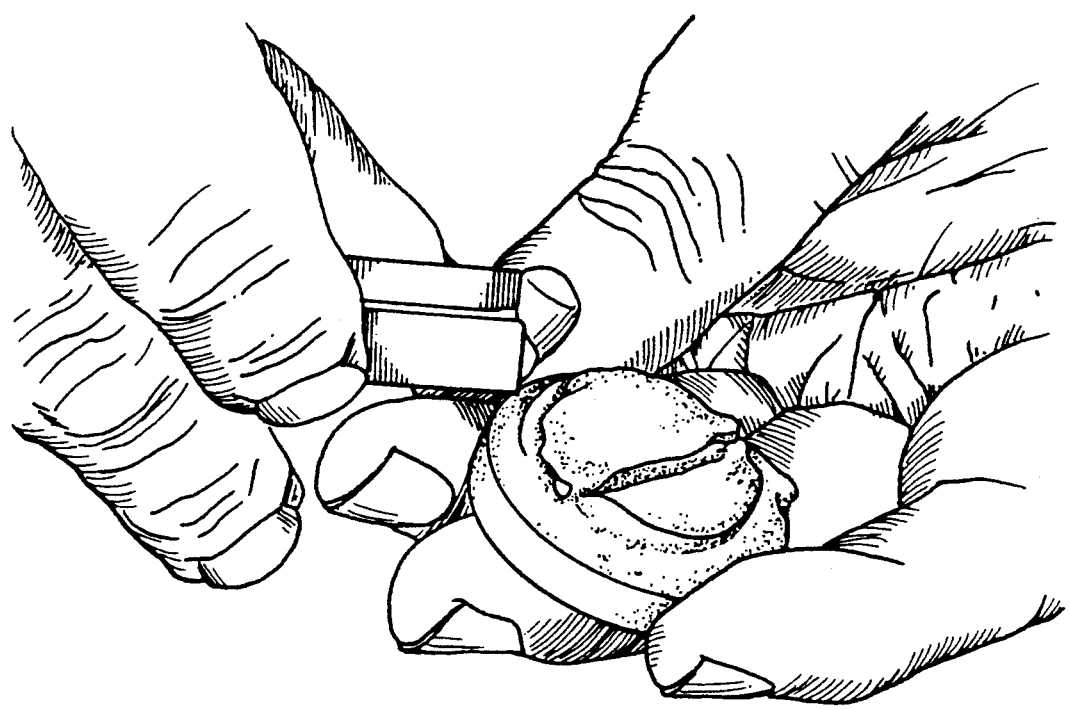
FIG. 13. Scleral acrylic adapted from package (extra light).
Figure 14:
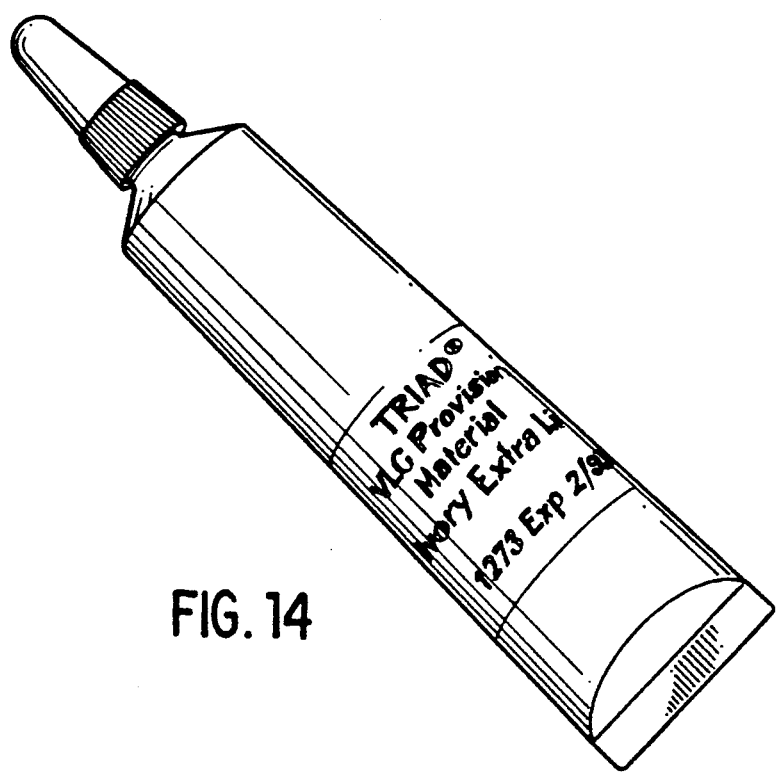
FIG. 14. Scleral acrylic (provisional material).
Figure 15:
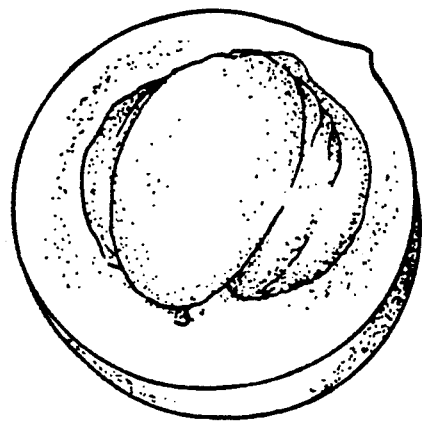
FIG. 15. Scleral portion cured under recommended modality.
Figure 16:
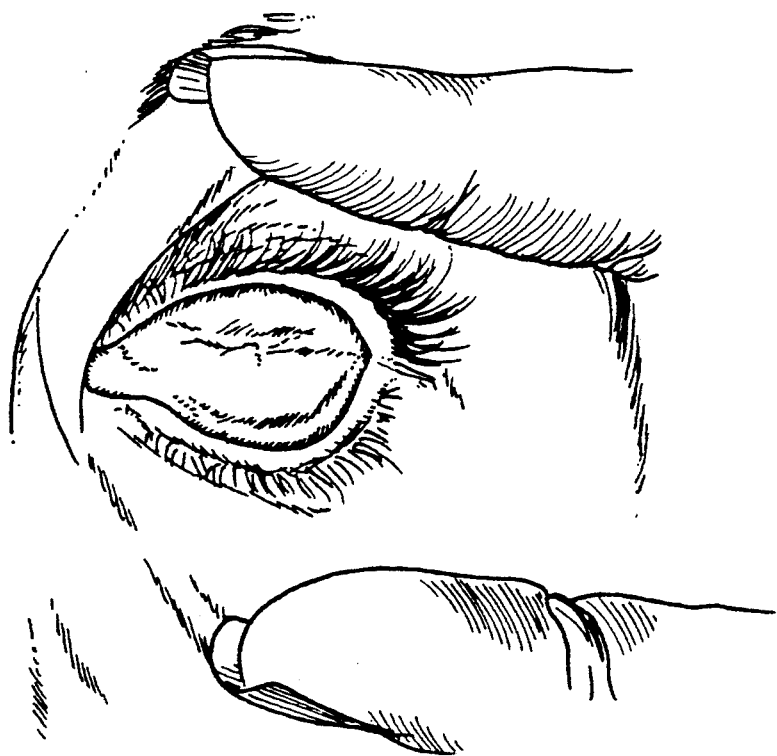
FIG. 16. Defect showing a very limited space placement.
Figure 17:
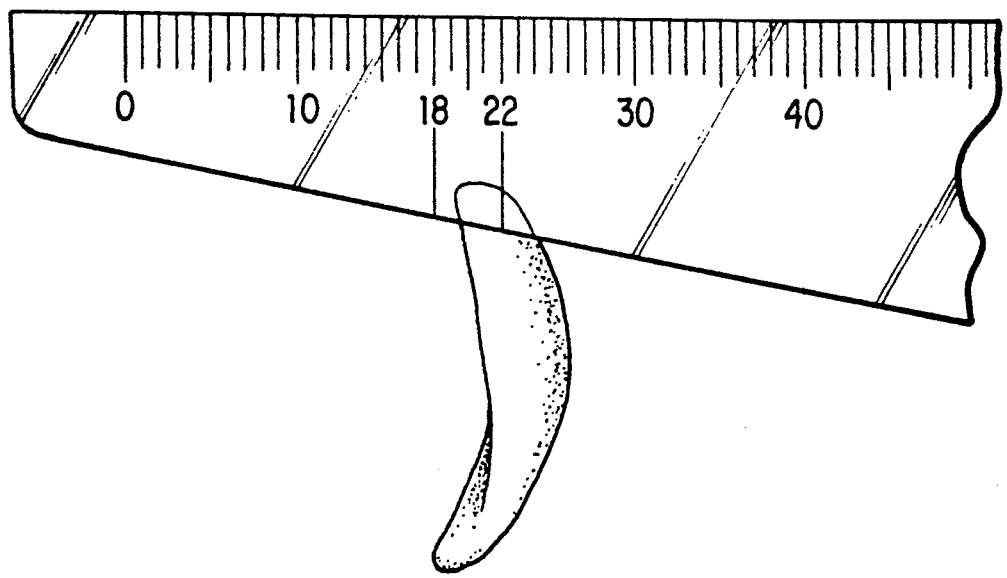
FIG. 17. Solera trimmed thin to accommodate for limited space.
Figure 18:
FIG. 18. Sclera fitting into defect.
Figure 19:
FIG. 19. Patient asked to go through facial muscle movements.
Figure 20:
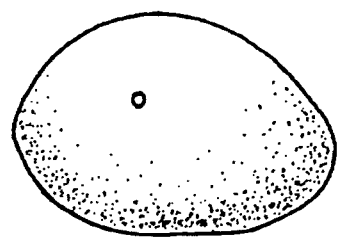
FIG. 20. Point of pupil center ascertained in patient's defect.
Figure 21:
FIG. 21. Sclera prepared for iris placement (area flattened).
Figure 22:
FIG. 22. Pupil disk tried.
Figure 23:
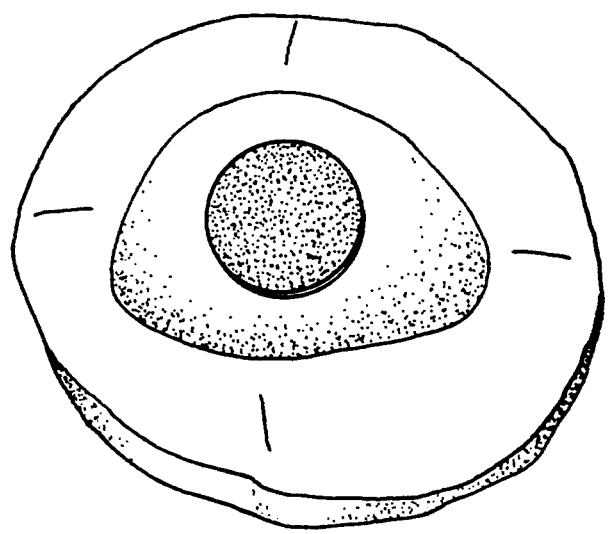
FIG. 23. Pupil disk cured.
Figure 24:
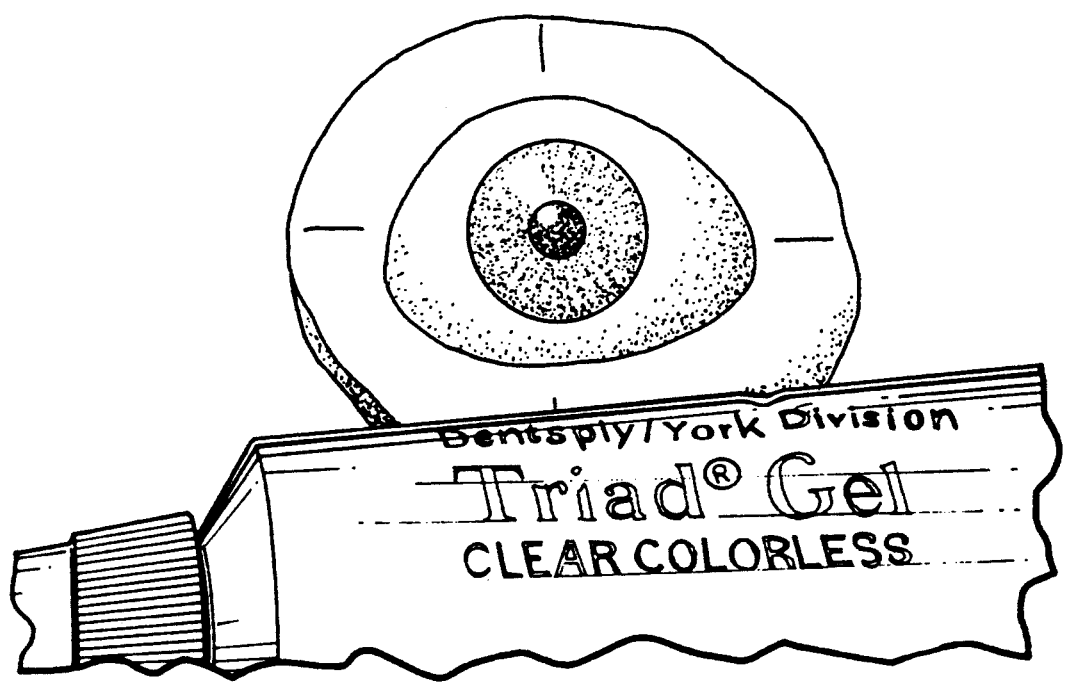
FIG. 24. Iris disk Attached with clear gel.
Figure 25:
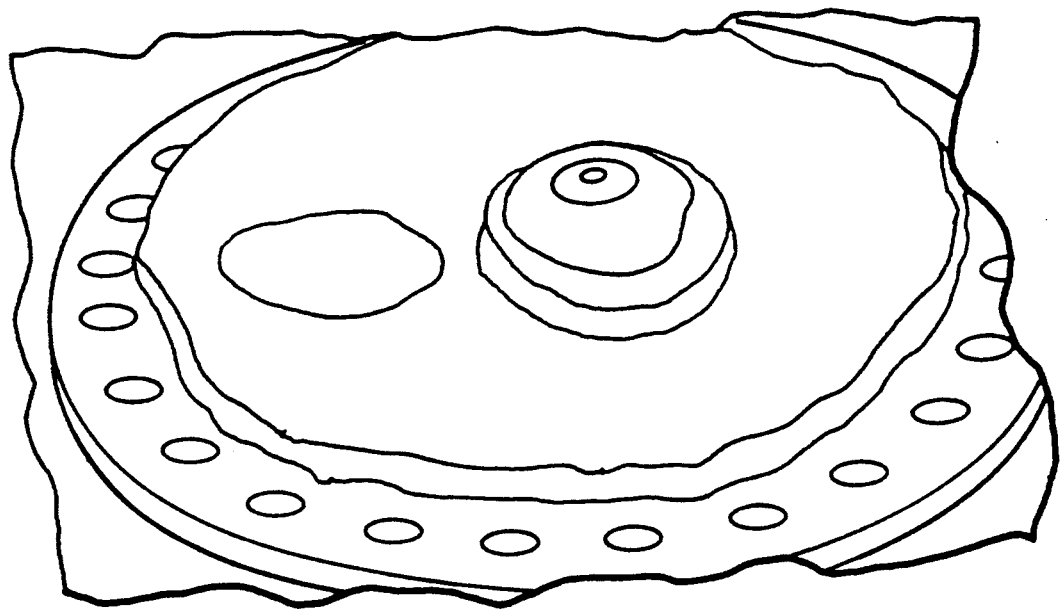
FIG. 25. Processed (cured) in curing unit.
Figure 26:
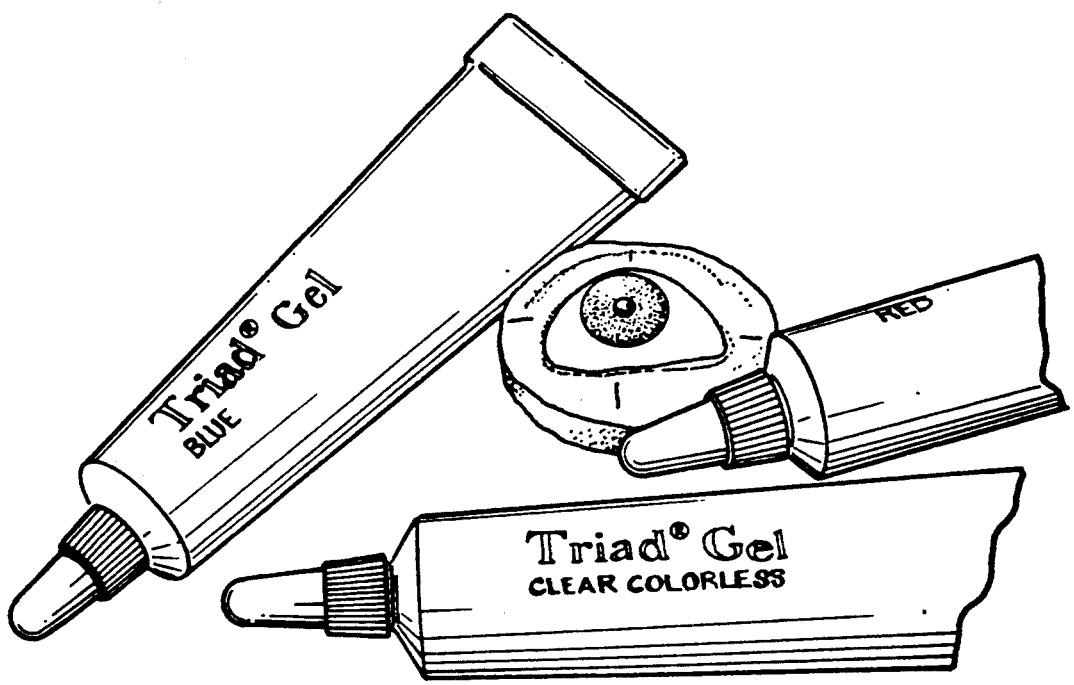
FIG. 26. Different scleral coloring gels (red, blue, pink).
Figure 27:
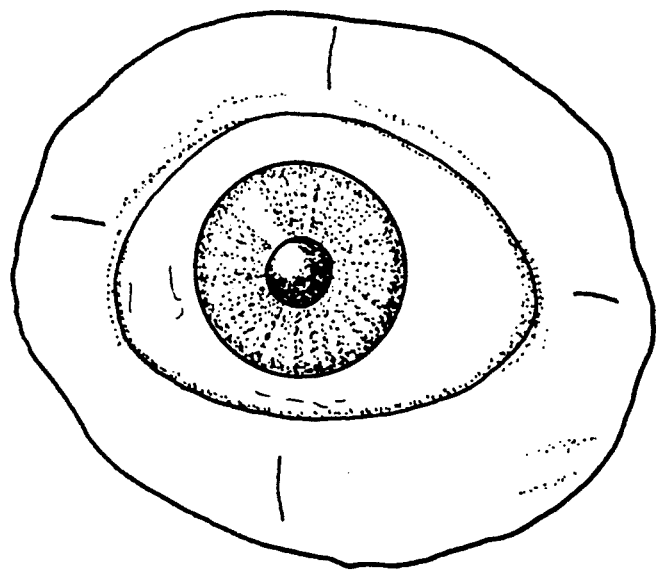
FIG. 27. Coloring applied rayon fibers placed, clear gel covered and cured.
Figure 28:
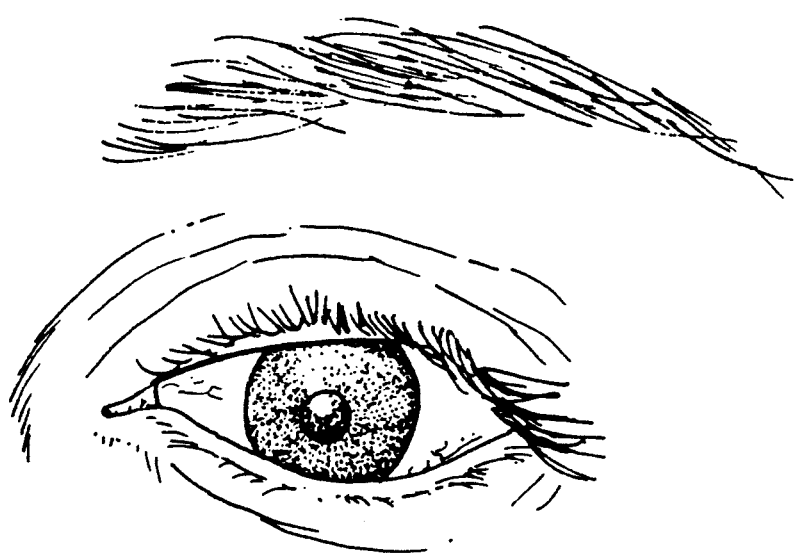
FIG. 28. Ocular placed with too much red coloring on intercantus area (error).
Figure 29:
FIG. 29. Patient with overcolored prosthesis.
Figure 30:
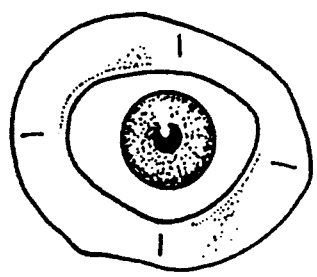
FIG. 30. Ocular with corrected coloring processed.
Figure 31:
FIG. 31. New recorrected ocular on patient.
Figure 32:
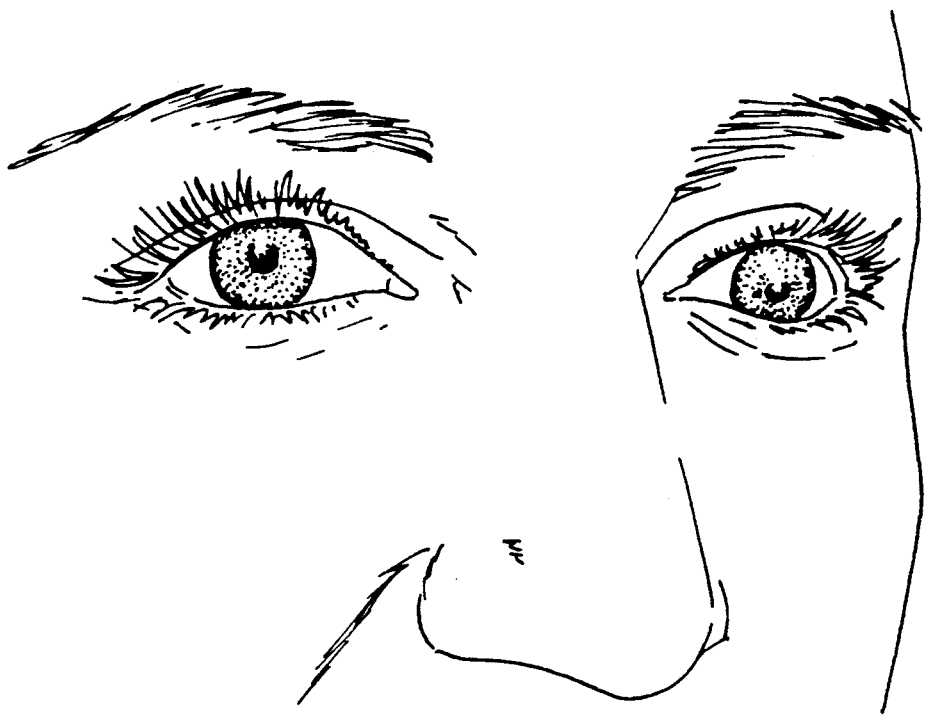
FIG. 32. Patient tested for proper ocular movement (Final step).

The following materials are used to construct a light-cured ocular prosthesis.
1—Dental stone
2—Iris disks with perforated middle or solid (Factor Two Lakeside Ariz.)
3—Ocular button with black pupil middle
4—Clear syrup solution 100/10 ratio monomer/polymer heat cure clear resin
5—Oil paints
6—Paint brushes 0, 00, 000 tip
7—Rayon fibers
8—VLC curing unit TRIAD 2000 model (used for this project) Dentsply International Inc., York, Pa.
9—VLC provisional tooth color material ivory light
10—VLC gel material clear colorless
11—MRA TRIAD model release agent
12—ABC TRIAD air barrier coating
13—Fast cure type II, class I monomer
14—Heat cure type I, class I monomer Procedure The first step is the construction of the sclera. A custom impression tray is constructed to simulate an actual clinical ocular (FIGS. 1-4). This mold enables the practitioner to consider the size and thickness for an optimum impression of the defect. The tissue side of the impression is poured with dental labstone (FIGS. 5-10) (Modern Materials Miles Inc., South Bend, Ind.). When hardened, the impression is removed and Model Release Agent MRA (Dentsply Inc., York, Pa.) is then applied. If a clear gel coating is needed around the prosthesis, then the clear gel is poured in the cast and cured at this time (FIGS. 11-12). The shade of sclera is then chosen, i.e., light, medium or dark, and the void left by the impression pattern is packed gently by finger pressure with VLC provisional material (FIG. 13-14). The cast with scleral material is then placed into a curing chamber on a rotating table and exposed to visible light for three minutes (FIG. 15). The solera is then light-cured again on the tissue side for another three minutes and removed from the turntable.

When cured, the rough edges are removed using the conventional methods. The solera is trimmed to the desired thickness and the external surface is toughened for the scleral tinting to adhere (FIGS. 16-32).

The thickness of the sclera is proportioned to the depth of the defect. The provisional material may be layered to construct an ocular of greater thickness or thinned to provide the desired eyelid support.

The Iris

The iris is painted with syrup solution (#4) and paint (#5) with the patient present. This solution is the only one that contains methyl-methacrylate. An advantage in using a perforated disk is that the disk will allow the VLC gel to adhere the pupil button and the iris to the sclera. Once the location of the iris is determined on the solera, the area of the sclera is flattened to accommodate the iris. A very light film of VLC clear gel adheres the iris to the sclera with a one minute light cure.

Painting Sclera

Using the syrup solution (#4), the sclera can be painted to obtain the desired tinting and rayon fiber placement to simulate the characteristics of the other eye. Clear gel with a faint blue hue can be used to cover some of this tinting and diluted red clear gel can be used near the innercantus area of the ocular. The appliance is returned to the chamber and cured for two minutes.

Ocular Pupil Button

While the tinting cure is still tacky, the ocular pupil button is coated with heat-cure monomer using a cotton swab. VLC clear gel is applied to the middle portion of the pupil and the iris, and cured for two minutes (if desired, the ocular button can be prepared with a slight cut in shoulder with a small burr around the base of the button itself, although this is not necessary because the gel offers a good bond after it is primed), (Andreopoulos et al., *Quintessence International*, 703–706, 1991). At this time the surface will still be tacky, the next step is to coat the entire surface with the desired thickness of clear gel to simulate the corneal shell. This corneal shell is light-cured for three minutes, then the entire corneal clear surface is coated with the Air Barrier Coating substance and cured for another three minutes. The ocular is finished and polished to obtain a smooth surface. The entire procedure of ocular construction can be accomplished in about two hours.

EXAMPLE 3

Toxicity Studies of Methylmethacrylate

Sufficient amounts of methylmethacrylate monomers are found to be present in heat-cured ocular prostheses to cause tissue irritation in sensitive patients. Stungis et al., (J. Pros. Dent. 22(4):425–428, 1969) describes hypersensitivity to acrylic resin in which the use of poly (methylmethacrylate) in appliances was necessarily discontinued.

Table I presents the Heath Hazard data from the material safety data sheet on methylmethacrylate published by the Aldrich chemical company.

TABLE I.

HEALTH HAZARD DATA FOR METHYLMETHACRYLATE, 99% ALDRICH CATALOG #M5590-9

ACUTE EFFECTS

Harmful if swallowed, inhaled, or absorbed through skin.

Vapor or mist is irritating to the eyes, mucous membranes and upper respiratory tract.

Causes skin irritation.

Symptoms of exposure may include burning sensation, coughing, wheezing, laryngitis, shortness of breath, headache, nausea and vomiting.

May cause allergic respiratory and skin reactions.
Prolonged exposure can cause:
Narcotic effect
Target organ(s):
Nose
Liver, kidneys

First aid

In case of contact, immediately flush eyes or skin with copious amounts of water for at least 15 minutes while removing contaminated clothing and shoes.

Assure adequate flushing of the eyes by separating the eyelids with fingers.

If inhaled, remove to fresh air. If not breathing give artificial respiration. If breathing is difficult, give oxygen.

Call a physician.
Remove and wash contaminated clothing promptly.
Discard contaminated shoes.

EXAMPLE 4

Construction of an Ocular Prosthesis Completely Free of Methylmethacrylate

In the construction of the light-cured ocular prosthesis of Example 2 the syrup solution #4 is the only solution that contains methyl-methacrylate and is used to paint the iris and solera. This colored area becomes covered with the polymerized clear gel that forms the corneal shell.

The use of this syrup solution may be eliminated by using a product of the Kulzer company of Germany called Dentacolor creactive colored urethane dimethacrylate. This material is free of methylmethacrylate and may be used for the painting of the iris and sclera, therefore, the resultant ocular prosthesis would be even more completely free of methylmethacrylate.

EXAMPLE 5

Construction of an Aesthetic Scleral Shell

An aesthetic scleral shell is an appliance made for a patient who due to trauma or a congenital defect is lacking an iris and a pupil. These VLC materials may be used to construct a clear shell which covers the defective eye and which is painted to mimic an iris and pupil. Scleral shells can be constructed to a desired thickness; they can be clear or scleral matched to the patient's other eye.

EXAMPLE 6

Use of Light-Cured VLC Materials in Association with Artificial Bone

The VLC materials may be used in association with artificial bone in, for example, the manufacture of a surgical stint or shell for the hydroxyapatite type of implant. A peg of VLC material with a magnet attached at an outer end is introduced into an implant. By virtue of the magnet attracting a second magnet which is implanted into a surgical template, the combination will attain desired results by being held in place on the surface of the appliance.

In a particular example, an enucleated patient suffers tissue atrophy and the surrounding muscles become rigid and develop scar tissue. With time, the eye is not able to be opened. Shells of VLC materials are made of increasing size for positioning into the eye to slowly train the muscles for movement.

The speed with which the VLC materials can be made into appliances facilitates their use as implants immediately during surgery. In an enucleation a surgical conformer can be constructed in a short time. This replacement device is essentially a temporary eyeball. Previous to the technology disclosed by the present invention, the replacement appliance would be constructed and inserted in a post surgical operation.

In view of the surprising and unexpected results obtained with ocular prostheses comprising the polymerized urethane dimethacrylate materials, it is now believed that those of skill in the ocular prosthesis art may now readily develop other types of polymers and procedures which have the desired characteristics.

While the invention is susceptible to various modifications and alternative forms, a specific embodiment thereof has been shown by way of example and therein was described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

The following citations are incorporated in pertinent part by reference herein for the reasons cited.

REFERENCES

Andreopoulos, A. G. et al., "Repairs with visible light-curing denture base materials" *Quintessence International*, 22:703-706, 1991.

Coates, J. B., (ed.) Surgery in World War II, Washington, D.C., Office of the Surgeon General, Department of the Army, 1957.

Dentsply ® Triad ™, Denture System Technique Manual, Dentsply Int'l Inc., York, Pa. (1984).

Eichhold, William A. et al., "Denture base acrylic resins: friend or foe?", *Compendium of continuing education Dent.*, vol XI, 12:720-725.

German Patent No. 4,011,053 to Kreiner, Oct. 10, 1991.

Gordon B., The ancient origins of artificial eyes., In: *Annals of Medical History*, ed. 3, ser. 2, New York, 1940.

Haug, P. A., Dissertatio de Oculo, Artificial Exbrepahro et *Ypobrepharo Tubingen*, Marz, 1749 (Bucreard David Mauchart).

Hayden, William J. "Flexural strength of microwave-cured denture baseplates", *General Dentistry*, Sept–Oct 1986, pp 367-371.

Heister L. Chirrurgie 1752, Das 63 Cap, Von Kunstlicher Augen S.; 581–582.

Helpful Recommendations for Denture Base Resins, L. D. Caulk Co., Dentsply. Int'l Inc., Milford, Del. (1978).

Hoefling, R. et al., "Processing of ocular and oral-facial prostheses with microwave irradiation", Fifth Annual American Anaplastology Association Meeting, University of Washington Dental School, Jun. 11, 1990.

Kahn, Z., et al., "The physical properties of a visible light-cured temporary fixed partial denture material", *J. Prosthetic Dent.*, 60:543–545, 1988.

Morrow RM, Rudd KD, Rhoads JE., Dental Laboratory Procedures, vol 1. Complete dentures. 2nd ed. St. Louis: CV Mosby Co., 1986; Chapter 9.

Ogle, R. E., et al., "A new visible light-cured resin system applied to removable prosthodontics" *J. Prosthetic Dent.*, 56:497–506, 1986.

Pare, A., Cimbroise, Paris, Orubres, 1561; 648–650.

Rudd, K. D. et al., "Dental Laboratory Procedures" Vol 1., Complete dentures, 2nd ed. St. Louis: CV Mosby Co., 1986; Chapter 9.

Stungis, T. E., et al., "Hypersensitivity to acrylic resin" *J. Pros. Dent.*, vol. 22, No. 4, pp. 425–428, Oct. 1969.

Trester W., The history of artificial eyes and the evolution of the ocularistic profession, *J. Am. Soc. Ocularists,* 1982; 5–13.

Triad ®, VLC Provisional Crown & Bridge Material, Dentsply. Int'l. Inc., York, Pa. (1986).

U.S. Pat. No. 3,937,680 entitled "Hydrophilic Gel Terpolymers from Hydrophilic N-Vinyl Monomers, Hydroxyalkyl Acrylates or Methacrylates and Polymerizable Unsaturated Carboxylic Acids" (1976).

What is claimed is:

1. An ocular prosthesis comprising a polymerized urethane dimethacrylate solid shell having a convex surface molded in the shape of the cornea and sclera of a normal human eye.

2. The ocular prosthesis of claim 1 wherein the solid shell is further defined as comprising silica and acylic resin beads.

3. An ocular prosthesis comprising:
   a solid shell simulating a sclera of a normal human eye, and
   a corneal shell coating simulating a cornea of a normal eye,
   wherein the shell and the shell coating comprise light-cured urethane dimethacrylate.

4. An ocular prosthesis comprising a light-cured urethane dimethacrylate solid shell having a convex surface molded in the shape of the sclera of a normal human eye.

5. The ocular prosthesis of claim 4 further comprising an iris disk, a pupil ocular button, and a corneal shell coating formed to represent the iris, the pupil and the cornea, respectively, of a normal human eye.

6. The ocular prosthesis of claim 5 wherein the corneal shell coating comprises light-cured urethane dimethacrylate.

7. The ocular prosthesis of claim 4 wherein the shell further comprises silica.

8. The ocular prosthesis of claim 4 wherein the shell further comprises acrylic resin beads.

* * * * *

UNITED STATES PATENT AND TRADEMARK OFFICE
CERTIFICATE OF CORRECTION

PATENT NO. : 5,326,346

DATED : July 5, 1994

INVENTOR(S) : Cortes, Aquileo L.

It is certified that error appears in the above-identified patent and that said Letters Patent is hereby corrected as shown below:

```
In claim 2, column 14, line 2, delete "acylic" and insert
--acrylic--, therefore.
```

Signed and Sealed this

Twentieth Day of September, 1994

Attest:

BRUCE LEHMAN

Attesting Officer

Commissioner of Patents and Trademarks